United States Patent
Campbell et al.

(10) Patent No.: US 6,518,460 B2
(45) Date of Patent: Feb. 11, 2003

(54) PROCESSES FOR PREPARING 3-ARYLSULFUR HYDROXAMIC ACIDS

(75) Inventors: Jeffrey Allen Campbell, Cheshire, CT (US); Lawrence Emerson Fisher, Mountain View, CA (US); Charles Alois Dvorak, Palo Alto, CA (US); Paul Leo McGrane, Mountain View, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/142,824

(22) Filed: May 8, 2002

(65) Prior Publication Data

US 2002/0133030 A1 Sep. 19, 2002

Related U.S. Application Data

(62) Division of application No. 09/991,143, filed on Nov. 9, 2001, now Pat. No. 6,470,573, which is a division of application No. 09/335,447, filed on Jun. 17, 1999, now Pat. No. 6,342,639.
(60) Provisional application No. 60/089,778, filed on Jun. 18, 1998.

(51) Int. Cl.$^7$ ............... C07C 323/07; C07C 323/13; C07C 323/16
(52) U.S. Cl. ............... 568/52; 568/56; 568/58
(58) Field of Search ............... 568/52, 56, 58

(56) References Cited

U.S. PATENT DOCUMENTS

| 3,966,848 A | 6/1976 | Schrider et al. |
| 5,672,599 A | 9/1997 | Robl |

FOREIGN PATENT DOCUMENTS

| EP | 0 780 386 A1 | 6/1997 |
| EP | 0 818 442 A2 | 1/1998 |
| WO | WO 92/08688 | 5/1992 |
| WO | WO 97/20824 | 6/1997 |
| WO | WO 97/24117 | 7/1997 |
| WO | WO 98/05635 | 2/1998 |
| WO | WO 98/13340 | 4/1998 |

OTHER PUBLICATIONS

R. Rynbrandt, et al., "The Oxidation of Aminocyclopropyl Sulfides," Tetrahedron Letters, vol. 19, 1972, pp. 1937–1940 (XP002116512—Elsevier Science Publishers, Amsterdam, NL).

P.L. Creger, "Metalated Carboxylic Acid.1.Alkylation," Journal of the American Chemical Society, vol. 89, May 10, 1967, pp. 2500–2501 XP002116513—American Chemical Society, Washington, D.C.

Cadogan, Quarterly Reviews, vol. 16: (1962) pp 208–239, "Oxidation of Tervalent Organic Compounds of Phosphorus".

Goralski, et al., Journal Organic Chemistry, vol. 42:18 (1977) pp 3094–3096, "A Convenient Synthesis of (Chloromethyl)thio Aromatics and (Chloromethyl)thio Heteroaromatics".

Hoffmann, et al., Journal American Chemical Society, (Communications to the Editor), vol. 78 Dec. 20, 1956, pp 6413–6414 The Reaction Between Triethyl Phosphite and Alkyl and Aryl–Sulfonyl Chlorides.

Klunder, et al., Journal of Organic Chemistry, vol. 52: (1987) pp 2598–2602, "A Convenient Synthesis of Sulfinate Esters from Sulfonyl Chlorides".

Mori, et al., Tetrahedron Letters, vol. 41:5 (1985) pp 919–925, "Biochemical Preparations of Both the Enantiomers of Methyl 3–hydroxypentanoate and Their Conversion to the Enantiomers of 4–Hexanolide, the Pheromone of *trogoderma glabrum*".

Pilard, et al., Tetrahedron Letters, vol. 38:21 (1997) pp. 3735–3738, "The Cathodic Cleavage of the S–P Bond. Synthesis and Electrochemical Behaviour of Sulfonamide Phosphorus Analogues".

Trost, et al., Journal Organic Chemistry, vol. 39:17 (1974) pp 2648–2650, "New Synthetic Reactions. A Convenient Approach to Methyl 3–Oxo–4–pentenoate".

Wada, et al., Bull. Chem. Soc. Jpn, vol. 62:3, 1989, pp 860–868, "New Synthesis of 2–Oxo–3–alkenylphosphonates and Hetero Diels–Alder Reactions with Vinyl Ethers Leading to 5–Substituted 2–Phosphinyl–2–cyclohexen–1–ones".

Primary Examiner—T. A. Sololn
(74) Attorney, Agent, or Firm—Rohan Peries

(57) ABSTRACT

This invention provides processes for the preparation of a compound of Formula I:

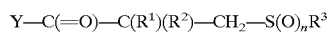

$$Y—C(=O)—C(R^1)(R^2)—CH_2—S(O)_nR^3$$

wherein:
Y is hydroxy or XONX, where each X is independently hydrogen, lower alkyl or lower acyl;
$R^1$ is hydrogen or lower alkyl;
$R^2$ is hydrogen, lower alkyl, aryl, aralkyl, cycloalkyl, cycloalkylalkyl, or $R^1$ and $R^2$ together with the carbon atom to which they are attached form a cycloalkyl or heterocyclo group;
$R^3$ is aryl; and
n is 0, 1 or 2.

The invention also provides novel aryl haloalkyl sulfide intermediates useful for the preparation of compounds of Formula I and novel methods of preparing aryl alkyl sulfides.

4 Claims, No Drawings

PROCESSES FOR PREPARING 3-ARYLSULFUR HYDROXAMIC ACIDS

CROSS-REFERENCE TO RELATED APPLICATION

This application is a divisional application of U.S. patent application Ser. No. 09/991,143, filed Nov. 9, 2001, now U.S. Pat. No. 6,420,573 which is a divisional of U.S. patent application Ser. No. 09/335,447, filed Jun. 17, 1999 now U.S. Pat. No. 6,342,639 which claims the priority benefit under 35 U.S.C. 119(e) of U.S. Provisional Application No. 60/089,778, filed Jun. 18, 1998, hereby incorporated by reference in its entirety.

BACKGROUND OF THE INVENTION

1. Field of the Invention

This invention relates to methods of preparing matrix metalloprotease inhibitors, particularly 3-arylsulfur hydroxamic acids.

2. Background Information

I. MMP Inhibitors

Matrix metalloproteases ("MMPs") are a family of proteases (enzymes) involved in the degradation and remodeling of connective tissues. MMP expression is stimulated by growth factors and cytokines in the local tissue environment, where these enzymes act to specifically degrade protein components of the extracellular matrix, such as collagen, proteoglycans (protein core), fibronectin and laminin. Excessive degradation of extracellular matrix by MMPs is implicated in the pathogenesis of many diseases, including rheumatoid arthritis, osteoarthritis, multiple sclerosis, bone resorptive diseases (such as osteoporosis), chronic obstructive pulmonary disease, cerebral hemorrhaging associated with stroke, periodontal disease, aberrant angiogenesis, tumor invasion and metastasis, corneal and gastric ulceration, ulceration of skin, aneurysmal disease, and in complications of diabetes.

Furthermore, inhibitors of MMP also are known to substantially inhibit the release of tumor necrosis factor (TNF) from cells and therefore may be used in the treatment of conditions mediated by TNF. Such uses include, but are not limited to, the treatment of inflammation, fever, cardiovascular effects, hemorrhage, coagulation and acute phase response, cachexia and anorexia, acute infections, shock states, restenosis, graft versus host reactions and autoimmune disease.

MMP inhibition is, therefore, recognized as a good target for therapeutic intervention. Consequently, inhibitors of MMPs provide useful treatments for diseases associated with the excessive degradation of extracellular matrix and diseases mediated via TNF and several MMP inhibitors are currently being developed for such uses.

One particular class of MMP inhibitors are the 3-arylsulfur hydroxamic acids described in EP 0 780 386 A1, published Jun. 25, 1997. This publication discloses MMP inhibitors of Formula I,

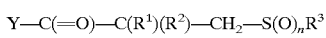

where n, Y, $R^1$, $R^2$ and $R^3$ are as described below in the Summary of the Invention.

WO 97/24117, published Jul. 10, 1997, discloses 3-aryl sulfur hydroxamic acids of formula, HON(H)—C(=O)—$C_p(R_1)(R_2)$—C($R_3$)($R_4$)—S(O)$_n$—$C_m(R_5)(R_6)$—Ar, where p, m, n and $R_1$, $R_2$, $R_3$, $R_4$, $R_5$, $R_6$ and Ar are as described in WO 97/24117.

WO 98/05635, published Feb. 12, 1998, discloses 3-arylsulfur hydroxamic acids of formula B—S(O)$_{0-2}$—$CHR^1$—$CH_2$—CO—NHOH, where B and $R^1$ are as described in in WO 98/05635.

WO 98/13340, published Apr. 2, 1998, discloses β-sulfonyl hydroxamic acids of HONHC(=O)—$CHR_2$—$CH_2$—S(O)$_2R_1$ where $R_1$ and $R_2$ are as described therein.

However, the processes disclosed in these publications for preparing 3-arylsulfur hydroxamic acids proceed via the nucleophilic attack of a thiol on the β-carbon of a carboxylate derivative, either displacing a leaving group at the β-carbon or performing a Michael reaction on an α,β unsaturated ester or acid. Thus, the disclosed processes are limited by the availability of the corresponding thiols and the β-substituted carboxylate derivatives and α,β unsaturated esters. This invention provides novel processes and novel intermediates that are not dependent on the availability of the reagents used in the above publications.

The use of 3-arylsulfonyl hydroxamic acids as MMP inhibitors is also described in WO 97/49679 A1, published Dec. 31, 1997.

II. Preparation of Aryl Alkyl Sulfides

Aryl haloalkyl sulfides are valuable intermediates in synthetic organic processes and they are commonly made by free radical halogenation of a precursor aryl alkyl sulfide. The aryl alkyl sulfide is in turn typically available via sulfonation of a precursor aryl hydrocarbon, reduction to an aryl thiol and alkylation of the thiol. It would be useful to have methods of directly converting arylsulfonyl derivatives to aryl methyl sulfides.

There have been various reports of the reactions between trialkyl phosphites and aryl sulfonyl derivatives. See, for example, R. W. Hoffman, T. R. Moore and B. J. Kagan, ("The Reaction between Triethyl Phosphite and and Alkyl and Aryl Sulfonyl Chlorides") *J. Am. Chem. Soc.*, 78:6413–6414 (1956); J. M. Klunder and K. Barry Sharpless, ("A Convenient Synthesis of Sulfinate Esters from Sulfonyl Chlorides") *J. Org. Chem.*, 52:2598–2602 (1987); and J. Cadogan ("Oxidation of Tervalent Organic Compounds of Phosphorous") *Quarterly Reviews*, 16:208–239 (1962). The reaction of benzensulfenyl chloride with triethylphosphite to yield ethyl phenyl sulfide has also been reported, T. Mukaiyama and H. Ueki, ("The Reactions of Sulfur-containing Phosphonium Salts") *Tetr. Lett.*, 35:5429–5431 (1967). Aryl sulfonyl chlorides have also been converted to aryl methyl sulfides in three steps by treatment of an aryl sulfonyl chloride with lithium diphenylphosphide, $Ph_2PLi$, to afford a P-diphenyl-aryl sulfophosphamide followed by cathodic reduction and methylation of the resulting aryl thiolate, J. Pilard and J. Simonet. ("The Cathodic Cleavage of the S-P Bond. Synthesis and Electrochemical Behaviour of Sulfonamide Phosphorous Analogues"), *Tetr. Lett.*, 38(21):3735–3738 (1997).

SUMMARY OF THE INVENTION

In one aspect, this invention provides processes for the preparation of a compound of Formula I:

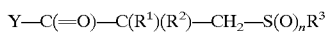

Formula I wherein:

Y is hydroxy or XONX—, where each X is independently hydrogen, lower alkyl or lower acyl;

$R^1$ is hydrogen or lower alkyl;

$R^2$ is hydrogen, lower alkyl, aryl, aralkyl, cycloalkyl, cycloalkylalkyl, or $R^1$ and $R^2$ together with the carbon atom to which they are attached form a cycloalkyl or heterocyclo group;

$R^3$ is aryl; and n is 0, 1 or 2;

comprising the steps of:

(1) alkylating a compound of Formula II,

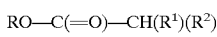

Formula II where R is alkyl or hydrogen, with an arylmethylthio derivative of Formula III, $ArSCH_2$—Z, wherein Ar is an aryl group and Z is a leaving group, to provide a compound of Formula IV, $RO$—$C(=O)$—$C(R^1)(R^2)$—$CH_2SAr$, and Formula IV (2) converting the compound of Formula IV to a compound of Formula I by replacing the group RO— with XONH— and optionally oxidizing the ArS group as necessary in either order.

The invention also provides novel aryl haloalkyl sulfide and aryl alkyl sulfide intermediates useful for the preparation of compounds of Formula I and novel methods of preparing aryl alkyl sulfides.

DETAILED DESCRIPTION OF THE INVENTION

Definitions

As used herein, the term "$(Cr_{p-q})$ alkyl" means a linear or branched fully-saturated hydrocarbon radical having p to q carbon atoms; for example, a "$C_{1-4}$ alkyl" means a linear or branched fully saturated hydrocarbon radical having one to four carbon atoms, such as methyl, ethyl, propyl, isopropyl, butyl, or tert-butyl.

Unless otherwise specified, the term "lower alkyl" means a $C_{1-4}$ alkyl radical.

As used herein, the term "$(C_{3-6})$ cycloalkyl" means a fully saturated cyclic hydrocarbon radical of three to six ring carbon atoms, e.g., cyclopropyl, cyclopentyl and the like.

As used herein, the term "lower acyl" refers to a group —C(=O)R, where R is a $(C_{1-4})$alkyl radical.

As used herein, the term "loweralkoxy" refers to a group —OR, where R is a $(C_{1-4})$alkyl radical.

As used herein, the term "$(C_{7-10})$alkoxy" refers to a group OR, where R is a $(C_{7-10})$alkyl radical.

As used herein, the term "aryl" means a monovalent monocyclic or bicyclic aromatic hydrocarbon radical of 6 to 10 ring atoms, and optionally substituted independently with one, two or three substituents selected from alkyl, haloalkyl, cycloalkyl, halo, nitro, cyano, optionally substituted phenyl, —OR (where R is hydrogen, alkyl, haloalkyl, cycloalkyl, optionally substituted phenyl), acyl, —COOR (where R is hydrogen or alkyl). More specifically the term aryl includes, but is not limited to, phenyl, 1-naphthyl, 2-naphthyl, and derivatives thereof.

As used herein, the term "arylene" means a divalent monocyclic or bicyclic aromatic hydrocarbon radical of 6 to 10 ring atoms, and optionally substituted independently with one, two or three substituents selected from alkyl, haloalkyl, cycloalkyl, halo, nitro, cyano, optionally substituted phenyl, —OR (where R is hydrogen, alkyl, haloalkyl, cycloalkyl, optionally substituted phenyl), acyl, —COOR (where R is hydrogen or alkyl). More specifically the term aryl includes, but is not limited to, 1,4-phenylene and 1,2 phenylene.

"Optionally substituted phenyl" means a phenyl group which is optionally substituted independently with one, two or three substituents selected from alkyl, haloalkyl, halo, nitro, cyano, —OR (where R is hydrogen or alkyl), —NRR' (where R and R' are independently of each other hydrogen or alkyl), —COOR (where R is hydrogen or alkyl) or —CONR'R" (where R' and R" are independently selected from hydrogen or alkyl).

"Heterocyclo" means a saturated monovalent cyclic group of 3 to 8 ring atoms in which one or two ring atoms are heteroatoms selected from N, O, or $S(O)_n$, where n is an integer from 0 to 2, the remaining ring atoms being C. The heterocyclo ring may be optionally fused to a benzene ring or it may be optionally substituted independently with one or more substituents, preferably one or two substituents, selected from alkyl, haloalkyl, cycloalkyl, cycloalkylalkyl, aryl, aralkyl, halo, cyano, acyl, monosubstituted amino, disubstituted amino, carboxy, or alkoxycarbonyl. More specifically the term heterocyclo includes, but is not limited to, pyrrolidino, piperidino, morpholino, piperazino, tetrahydropyranyl, and thiomorpholino, and the derivatives thereof.

"Leaving group" has the meaning conventionally associated with it in synthetic organic chemistry i.e., an atom or group capable of being displaced by a nucleophile and includes halogen, alkanesulfonyloxy, arenesulfonyloxy, amino, alkylcarbonyloxy, arylcarbonyloxy, such as chloro, bromo, iodo, mesyloxy, tosyloxy, trifluorosulfonyloxy, N,O— dimethylhydroxylamino, acetoxy, and the like.

In one aspect, this invention provides a process for the preparation of a compound of Formula I:

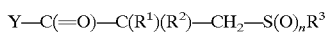

Formula I wherein:

Y is hydroxy or XONX, where each X is independently hydrogen, lower alkyl or lower acyl;

$R^1$ is hydrogen or lower alkyl;

$R^2$ is hydrogen, lower alkyl, aryl, aralkyl, cycloalkyl, cycloalkylalkyl, or $R^1$ and $R^2$ together with the carbon atom to which they are attached form a cycloalkyl or heterocyclo group;

$R^3$ is aryl; and n is , 1 or 2;

comprising the steps of:

(1) alkylating a compound of Formula II,

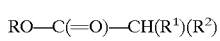

Formula II where R is alkyl or hydrogen, with an arylmethylthio derivative of Formula III, $ArSCH_2$—Z, wherein Ar is an aryl group and Z is a leaving group, to provide a compound of Formula IV, $RO$—$C(=O)$—$C(R^1)(R^2)$—$CH_2SAr$ and Formula IV (2) converting the compound of Formula IV to a compound of Formula I by replacing the group RO— with XONH— and optionally oxidizing the ArS group as necessary in either order.

Unlike the methods disclosed in EP 0 780 386 A1, published Jun. 25, 1997, WO 97/24117, published Jul. 10, 1997, WO 98/05635, published Feb. 12, 1998 and WO 98/13340, published Apr. 2, 1998, for the synthesis of 3-arylsulfur hydroxamic acids, the processes of the present invention proceed via the alkylation of the α-carbon of a carbonyl group with a halomethyl aryl sulfide. The invention also provides novel halomethyl aryl sulfides, such as chlorophenoxyphenyl chloromethyl sulfide and methods for their preparation. Thereby, the inventors are able to prepare compounds of Formula I by novel processes not previously available.

These reaction processes are shown in Scheme A, below.

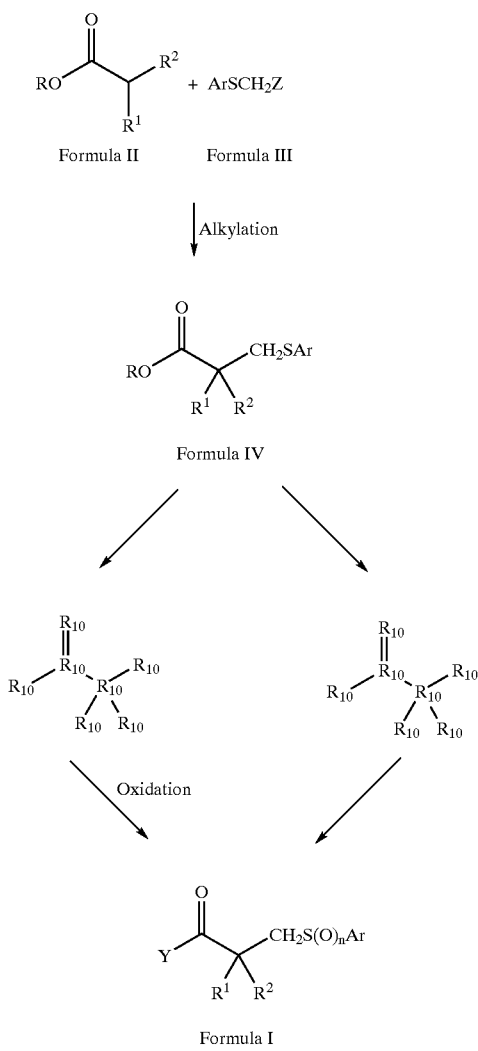

n = 1 or 2

Compounds of Formula IV may be converted to compounds of Formula I by conversion of the carboxyl group to a group —C(=O)—L where L is a leaving group under nucleophilic displacement conditions followed by displacement of L with hydroxylamine (or an alkylated derivative). The resulting hydroxamic acid is then oxidized as necessary to give the desired sulfoxide or sulfone. Oxidation to the sulfoxide is accomplished by treatment with mild oxidizing agents such as sodium or potassium metaperiodate or one equivalent potassium peroxymonosulfate (Oxone™). Other oxidants that may be used include peracids, (e.g. performic or peracetic acid) or sodium perborate/organic acid mixtures (e.g. performic or peracetic acid). The reaction may be halted at the sulfoxide stage by limiting the quantity of reagents, temperature and reaction time. Further oxidation to the sulfone is accomplished by treatment under more vigorous conditions with organic peracids such as m-chloroperbenzoic acid or two equivalents of sodium peroxymonosulfate. Alternatively, other oxidizing agents such as perborates, e.g., sodium perborate, in a carboxylic acid solvent such as formic, acetic or propionic acid may be used. These last two steps may also be reversed, i.e., oxidation of the sulfur moiety may precede conversion of the acid to the hydroxamate. However, overall yields are usually higher with the former sequence.

Compounds of Formula II, RO—C(=O)—CH($R^1$)($R^2$), can be purchased from commercial suppliers or are readily available by published procedures known to one of skill in the art. See, for example, EP 0 780 386 A1.

Compounds of Formula III, ArSCH$_2$—Z, are made by oxidation of the precursor arylmethylthioether. Compounds ArSCH$_2$Cl are made by oxidation with sulfuryl chloride in aprotic solvents such as methylene chloride, t-butylmethyl ether or hexane. The oxidation may be done at room temperature or at lower temperatures, e.g., from about 0–10° C. Other reagents, such-as N-chlorosuccinimide, may also be used. Compounds ArSCH$_2$Br are made by oxidation with sulfuryl bromide or other reagents such as N-bromosuccinimide.

Compounds of Formula III, ArSCH$_2$—Z, where Z is chloro or bromo may also be made from the corresponding thiol as shown below:

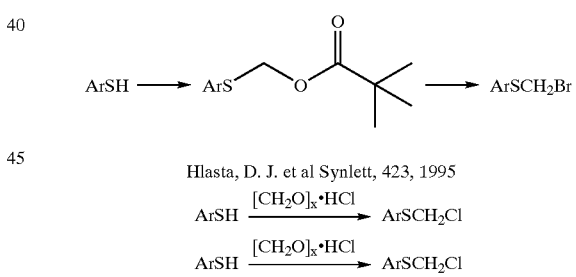

Hlasta, D. J. et al Synlett, 423, 1995

ArSH $\xrightarrow{[CH_2O]_x \cdot HCl}$ ArSCH$_2$Cl

ArSH $\xrightarrow{[CH_2O]_x \cdot HCl}$ ArSCH$_2$Cl

Arylmethylthioethers are generally available either from commercial vendors or published literature procedures. For example, they may be made by sulfonylating an aryl compound to the corresponding sulfonic acid, reducing the sulfonic acid to a thiol and methylating the thiol.

Alternatively, as shown in Scheme B, the inventors have unexpectedly discovered that arylsulfonyl halides can be converted directly to arylmethylthioethers in one step by treatment with trimethylphosphite. The conversion proceeds best if the trimethylphosphite treatment is followed by treatment with a base. Either an organic base such as an alkylamine (e.g. triethylamine) or a hydroxylic base such as an alkali metal hydroxide or an alkaline earth metal hydroxide may be used. However, the conversion may also be accomplished, albeit in somewhat lower yield, without the addition of a base. In such processes, the yield of the aryl methyl sulfide may be increased by heating to elevated temperatures, e.g., as high as about 100° C., preferably as high as about 130° C. (internal temperature). Consequently, the invention also provides a novel method of preparing aryl methyl sulfides by directly reducing/alkylating an arylsulfonyl halide with trimethyl phosphite.

Scheme B

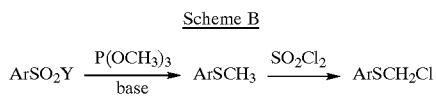

The method is particularly useful for forming compounds of formula $ArSCH_3$, wherein Ar has the formula $—Ar^1—A—Ar^2$, where $Ar^1$ and $Ar^2$ are phenyl rings, each independently optionally substituted and A is a bond, $CH_2$ or —O—, and more particularly where, A is oxygen, $Ar^1$ is phenyl and $Ar^2$ is 4-chlorophenyl.

Subsequent halogenation of $ArSCH_3$ then provides key intermediates of formula $ArSCH_2$—X where X is halo. Useful key intermediates include those where Ar is $—Ar^1—A—Ar^2$, wherein $Ar^1$ and $Ar^2$ are independently optionally substituted phenyl, X is halo, A is oxygen, or $CH_2$. A particularly useful intermediate is that wherein $Ar^1$ is phenyl, $Ar^2$ is halophenyl, and A is oxygen. useful intermediate is that wherein $Ar^1$ is phenyl, $Ar^2$ is halophenyl, and A is oxygen.

Alkylation of a compound of Formula II with a compound of Formula III may be accomplished by conditions known to one of skill in the art such as converting a compound of Formula II to an enolate or enol followed by reaction with a compound of Formula III. Other conditions include forming the dianion of the acid (i.e., compound of Formula II where R=H) by treatment with two equivalents of a base such as lithium diisopropylamide or lithium hexamethyldisilazide and alkylating with one equivalent of a compound of Formula III.

In one embodiment, a compound of Formula II was converted to a silylketene acetal as shown in Reaction Scheme C (where Silyl represents a silyl group), followed by Mukaiyama coupling of the acetal with a compound of Formula III. The coupling is generally done in an anhydrous aprotic solvent such as a halocarbon or hydrocarbon (methylene chloride, chloroform, benzene, toluene etc.) in the presence of a Lewis acid such as zinc chloride, zinc bromide, zinc iodide, ferric bromide or titanium tetrachloride. Silylketene acetals may be readily prepared from compounds of Formula II by procedures such as those described in C. Ainsworth, F. Chen, Y. N. Kuo "Ketene Alkyltrialkylsilyl Acetals: Synthesis, Pyrolysis and NMR Studies") *J. Organometallic Chem.*, 46:59–87 (1972). A variety of silyl protecting groups, e.g., t-butyldimethylsilyl, trimethylsilyl, etc. may be used. Silylketene acetals can be formed from either the ester (R=alkyl) or acids (R=H) of Formula II. Formation of the silylketene acetal from the acid may be accomplished using two equivalents of base and quenching with two equivalents of the silylating, reagent. Subsequent alkylation with a compound of Formula III followed by a hydrolytic work up then directly yields a carboxylic acid of Formula IV. Reagents that may be used to form the silylketene acetal include trimethylysilyl triflate, trimethylsilyl chloride or bromide, tert-butyldimethylsilyl chloride and bis-trimethylsilyl acetamide.

SCHEME C

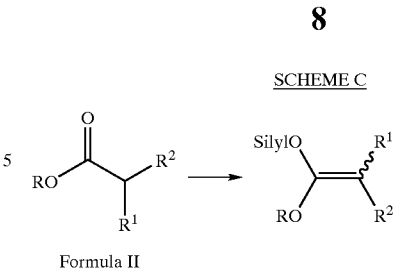

Formula II

Alternatively, an enolate of a compound of Formula II may be directly alkylated with a compound of Formula III, thus avoiding the intermediacy of the silylketene acetal. The enolate is formed under standard conditions, by treatment with a non-nucleophilic organic base such as lithium diisopropylamide or lithium hexamethyldisilazide, or a metal hydride such potassium hydride, under anhydrous conditions, typically at room temperature, in a polar aprotic solvent such as tetrahydrofuran, dimethoxyethane or glyme and the like. Subsequent addition of a compound of a Formula III followed by heating if necessary to reflux temperatures, e.g., 60–80° C., provides an alkylated product of Formula IV. The enolate may also be formed from the corresponding α-bromoester of a compound of Formula II by treatment with zinc to form the zinc enolate which can then be alkylated.

Though the processes described herein may be used to prepare a variety of 3-arylsulfur hydroxamic acids and their corresponding carboxy and ester derivatives, they are particularly useful for preparing compounds of Formula I wherein the aryl group Ar is of the formula $—Ar^1—A—Ar^2$, wherein $Ar^1$ and $Ar^2$ are phenyl rings, each independently optionally substituted and A is a bond, $—CH_2—$ or —O—.

Other useful compounds that may be made by the methods of the invention include compounds of Formula I where $R^1$ and $R^2$ together with the carbon atom to which they are attached form a cycloalkyl or heterocyclo group, particularly a tetrahydropyranyl group.

Additional useful hydroxamic acids that may be prepared include those that are α, α-disubstituted, i.e., neither $R^1$ nor $R^2$ are hydrogen.

Utility and Administration

As described earlier, the compounds made by these processes are MMP inhibitors, useful in treating a variety of diseases as disclosed in EP 0 780 386 A1, published Jun. 25, 1997; WO 97/24117, published Jul. 10, 1997; and WO 98/05635, published Feb. 12, 1998.

The following preparations and examples are given to enable those skilled in the art to more clearly understand and to practice the present invention. They should not be considered as limiting the scope of the invention, but merely as being illustrative and representative thereof.

Abbreviations used in the examples are defined as follows: "DMF" for dimethylformamide, "NaOH" for sodium hydroxide, "DMSO" for dimethylsulfoxide, "PTLC" for preparatory thin layer chromatography, "EtOAc" for ethyl acetate, "LDA" for lithium diisopropylamide and "TMSCl" for trimethylsilylchloride.

EXAMPLE

Synthesis of 4-[4-(4-chlorophenoxy) phenylsulfonylmethyl]-4-(N-hydroxycarboxamido) Tetrahydropyran Scheme D shows a representative method of this invention for the preparation of 14, 4-[4-(4-chlorophenoxy) phenylsulfonylmethyl]-4-(N-hydroxycarboxamido) tetrahydropyran, a compound of Formula I, wherein:

Y is NHOH;

R¹ and R² together with the carbon atom to which they are attached represent a tetrahydropyran-4-yl group; and R³ is 4-chlorophenoxyphenyl.

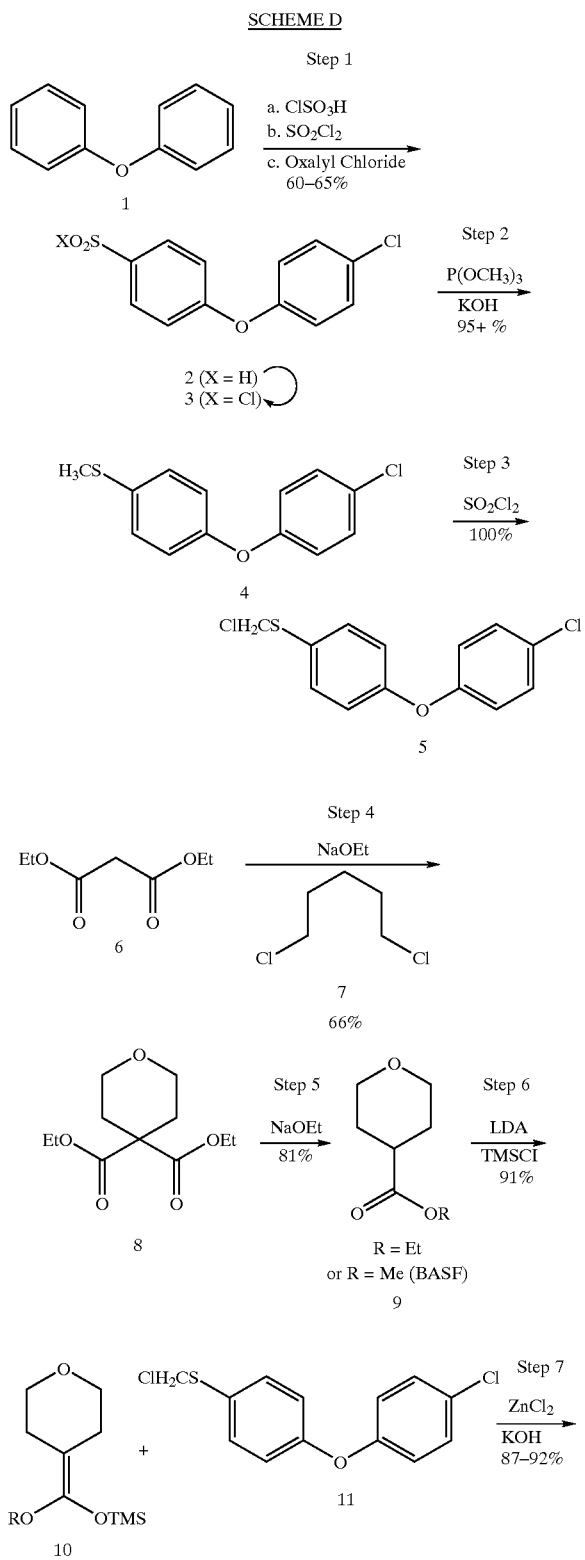

Although Scheme D is directed towards the synthesis of a specific 3-arylsulfur hydroxamic acid, it is to be understood that a similar set of reactions can be used to prepare other arylsulfur hydroxamic acids, carboxylic acids and esters by substituting appropriate starting materials and reagents as outlined in Reaction Schemes A–C.

A. Preparation of 4-(4-Chlorophenoxy)phenyl Chloromethyl Sulfide

Step 1

Diphenylether 1, is available from Aldrich (Milawaukee, Wis.) and can be converted to 4-(4'-chlorophenoxy)phenyl sulfonylchloride, compound 3, using known procedures, such as described in WO 97/20824.

Step 2

4-(4'-Chlorophenoxy)phenyl sulfonyl chloride (3.0 kg), 3, was dissolved in three liters of toluene and the solution was added dropwise, with stirring, to 3.6 kg of trimethyl phosphite which had been preheated to 60° C. The reaction was exothermic and the reaction was allowed to heat to 80°–90° C. during the addition. Thin layer chromatography indicated a mixture of the desired thioether and two baseline products. The mixture was refluxed until the pot temperature rose to ~130° C. The mixture was cooled to ~60° C. and 1 liter of methanol was added. Potassium hydroxide solution (4.5 kg of 45% aqueous solution) was added dropwise, slowly, with rapid stirring to the reaction mixture. The addition was very exothermic and the pot temperature was controlled to 65°–80° C. The mixture was then refluxed for 2 hrs. More toluene (6 liters) was added and the mixture cooled to ~60° C. The lower aqueous layer was separated and the organic layer washed with 3 liters of water. The organic layer was stripped to a low volume and 9 liters of isopropanol charged to the hot mixture. The solution was distilled until ~3.5 liters of distillate had been collected. The mixture was held at 45° C. for several hours and was then cooled to ~–10° C. and stirred several hours. The white, crystalline product was collected, washed with cold isopropanol and dried to yield 1.9 kg of 4-(4'-chlorophenoxy)phenyl methyl sulfide, 4.

Step 3

Into a separate reactor was charged 4-(4'-chlorophenoxy) phenyl methyl sulfide, 4, and $CH_2Cl_2$ (26 Kg). The resultant solution was cooled to less than 10° C. and then treated with $SO_2Cl_2$ at such a rate so that the temperature did not exceed 10° C. (30 min. required for the addition). An additional 2 Kg of $CH_2Cl_2$ was used to rinse in the $SO_2Cl_2$. After stirring for 1 h, the mixture was warmed to room temperature (degassing occurs) and then further warmed to reflux for 30 minutes. Upon cooling to room temperature, the product solution was washed with water (15.5 Kg) and then with brine (10.3 Kg). The stirred organic solution was then treated with a slurry of $MgSO_4$ (2.6 kg) in $CH_2Cl_2$ (5 kg). The drying was allowed to proceed overnight and the mixture was filtered to remove the drying agent. The solids were washed with $CH_2Cl_2$ (20.7 kg) and the combined organics were concentrated to effect azeotropic drying (38 kg of distillate collected, Karl Fischer shows 0.026% water in concentrate). The product was treated with $CH_2Cl_2$ (19.8 kg) and then was reconcentrated (19.8 kg distillate, Karl Fischer now at 0.014%). HPLC analysis showed 94.7% 4-(4'-chlorophenoxy)phenyl chloromethyl sulfide, 5.

B. Preparation of Silylketene Acetal

Steps 4 and 5

Tetrahydropyran-4-carboxylic acid ethyl ester, 9, was prepared from commercially available diethylmalonate via steps 4 and 5 using known literature procedures as described in for example, U.S. Pat. Nos. 5,412,120; 5,414,097; and EP584663 A2.

Step 6

To a nitrogen purged reactor was charged 26.8 kg (67.37 mole) of a solution of LDA. This was cooled to −15° C. and then a mixture of TMSCl (7.32 kg, 67.37 mole) and tetrahydropyran-4-carboxylic acid ethyl ester, 9, (10.32 kg, 65.3 mole) was added at such a rate that the temperature did not exceed −10° C. (1 h addition time). An additional 0.2 kg of TMSCl was added in one portion. The resultant mixture was heated to 20° C. and, after 4 h, a vacuum of 28 mm Hg was applied. The mixture was heated to 65° C. to remove volatiles. Toluene (11.95 kg) was added and the distillation continued. When no more distillate collected, the mixture was cooled to 25° C. A slurry of celite (2.7 kg) in hexane (20.6 kg) was added. After stirring 1 h, the mixture was filtered through a precoated Nutsche filter (1.5 kg of celite in 5 kg of hexane for precoat). The reactor was rinsed with hexane (11 kg), and this was used to rinse the filter. The combined organics were concentrated to an oil using 19–25 mm Hg and mild heating. The concentrate was transferred to a nitrogen purged storage vessel with the aid of $CH_2Cl_2$ (7 kg) to give 17.5 kg of a solution of silylketene acetal 10.

C. Preparation of 4-[4-(4-chlorophenoxy) phenylsulfonylmethyl]-4-(N-hydroxycarboxamido) Tetrahydropyran

Step 7

90% of the silylketene acetal solution from Step 6 was charged to the reactor containing 4-(4'-chlorophenoxy) phenyl chloromethyl sulfide 5, followed directly by a slurry of $ZnCl_2$ (0.59 kg, 4.34 mole) in $CH_2Cl_2$ (5 kg). The red reaction mixture was heated to reflux for 14 h (minimal heating required during first 1 h due to exotherm), at which point HPLC showed about 10% starting material. The remaining 10% of the ketene acetal was added and the mixture was heated at reflux with collection of the $CH_2Cl_2$ to a pot temperature of 68° C. HPLC analysis of an aliquot showed <1% starting material. Ethanol (15.5 kg), water (20.6 kg), and 45% KOH (20.3 kg) were added to the concentrated product mixture. The two phase mixture was stirred at 65° C. overnight (17 h) and was then warmed to a pot temperature of 90° C. to complete the saponification and to distill the ethanol. The mixture was cooled to 60–65° C. and hexane (41 kg) was added. After stirring 10 min. and then allowing layer separation, the lower layer was transferred to another reactor containing water (24 kg) and 37% HCl (21.6 kg). Simultaneous with this transfer, EtOAc (134.5 kg) was pumped to the receiving reactor. The hexane solution was washed once with 65° C. water (25 liters) which was then transferred to the receiving reactor. This reactor now contained an EtOAc solution of the product acid and a lower aqueous layer. The lower layer was separated and replaced with 50 L of 65° C. water. After stirring briefly, the layers were separated. The organic solution was concentrated as much as possible using partial vacuum. $CH_3CN$ (93.5 kg) was added and distillation continued at atmospheric pressure to a final volume of 90 liters. The mixture was cooled over 8 h to 5° C. and was held there 8 h. The solids were collected on a filter and were washed with $CH_3CN$ (15 kg) and hexane (15.5 kg). After drying at 78° C. and 24 mm Hg to constant mass, there was obtained 16.34 kg of the product acid, 12, as a dense, slightly off-white solid. HPLC purity was 99%.

Step 8

A clean, dry 100 gallon reactor was charged with 4-carboxy-4-{4-(4-chlorophenoxyphenyl) thiomethyl}tetrahydropyran 12 (15.45 kg, 40.7 moles). To this reactor was added dichloromethane (77.2 L, 102 kg). The suspended carboxylic acid was chilled to 0–5° C. under $N_2$ with agitation. A catalytic amount of N,N-dimethylformamide (0.1 l) was charged, followed by slow addition of oxalyl chloride (5.3 kg, 3.6 L). The contents of the reactor were agitated and the internal temperature was allowed to rise to ambient over a 4–12 hour period to allow conversion to the acid chloride. Another clean, dry 100 gallon reactor was charged with tert-butanol (26.8 kg, 34.5 L), tetrahydrofuran (75.4 kg, 84 L) and hydroxylamine (50 aqueous, 17 kg, 15.8 L). The contents of this reactor were agitated at ambient temperature. The contents of the reactor containing the acid chloride were chilled to 0–5° C. Slow addition of the hydroxylamine solution is begun. The rate of addition was regulated such that the internal temperature of the acid chloride solution does not rise above 10° C. When the addition is complete, the contents of the reactor containing the newly formed hydroxamic acid were warmed to 20–25°. After a check for reaction completeness (HPLC or TLC), the solvent was removed in vacuo keeping the contents of this reactor below 45° C. When little solvent is left to distill, the reactor was charged with acetonitrile (48.6 kg, 61.7 L). The contents were heated to reflux, and water (61.7 L) was added over a period of 30–50 minutes. The contents of the reactor were cooled to 0–5° C. over a period of 2–4 hours and slowly agitated for 4–14 hours. The solid hydroxamic acid 13, was collected by filtration and washed with water. Typically, the wetcake so obtained is not dried but used as is. However, drying can be accomplished in vacuo at ca 50° C. The solid (21.5 kg wet, 14.45 kg dry, 90.1%) was 99.8% pure by area normalization HPLC.

Step 9

A clean, dry 100-gallon reactor was charged with oxone® (potassium peroxymonosulfate, 37.07 kg, 60.3 moles). Deionized water was added (88.3 kg) and the contents of the reactor were agitated and heated (to ca. 35–40° C.) to dissolve the oxone. Another clean, dry 100 gallon reactor was charged with the hydroxamic acid, 13, (21.18 kg waterdamp cake, 14.45 dry weight, 36.7 moles) and dissolved in N-methyl-2-pyrrolidinone (100.5 kg) with agitation. The contents of this reactor were heated to 30–35° C. The aqueous oxone™ solution was added to the reactor containing the hydroxamic acid at such a rate that the internal temperature did not exceed 49° C. After the addition of oxone™ was complete, the mixture was assayed by HPLC and TLC. When the reaction was complete, typically in 0 to 1 hour post addition (HPLC data area normalization purity is typically >98.5% desired product) the product was treated with deionized water (25 kg) and cooled to 20° C. Crystallization of the crude product typically occurred at 20–25° C. (22° C. in this example). The mixture was then cooled to 5° C. and stirred for 10–14 hours (12 in this example). The precipitated product was collected by filtration and washed well with deionized water followed by hexanes. This wet cake (47.9 kg) was charged into a clean, dry, residue free 100-gallon reactor. Ethyl acetate (140 kg) was charged to the solid followed by deionized water (120.6 kg). The contents of the reactor were agitated and heated (to ca 60° C.). Agitation was stopped and the layers were allowed to separate. The aqueous layer was separated. Optionally, this can be followed by an aqueous $NaHCO_3$ wash and water wash. The organic layer was filtered through a 5–10 μ cotton filter into a clean, dry, residue free reactor. The mixture was concentrated in vacuo to approximately 50% (ca 50 L) of the starting volume. The solid was separated and recrystallized from ethyl acetate after heating to approximately 70° C. and cooling to 5° C. The solid was collected by filtration in a clean dry filter and dried at 40–45° C. under a nitrogen stream (an agitated filter was used for this example). 11.82 kg of final product, 4-[4-(4-chlorophenoxy)phenylsulfonylmethyl]-4-(N-hydroxycarboxamido) tetrahydropyran, compound 14, was obtained in 75.6% yield (99.8% pure by area normalization HPLC) upon vacuum drying.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A process of preparing a compound of Formula $ArSCH_3$, wherein Ar is an aryl group, said process comprising contacting a compound of Formula $ArSO_2Cl$ with trimethyl phosphite to produce the compound of Formula $ArSCH_3$.

2. The process of claim 1, wherein Ar is of the formula:

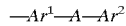

wherein each of $Ar^1$ and $Ar^2$ is independently an optionally substituted phenyl, and A is a bond, —$CH_2$— or —O—.

3. The process of claim 2, wherein A is oxygen; $Ar^1$ is phenyl; and $Ar^2$ is 4-chlorophenyl.

4. The process of claim 1, further comprising adding a base.

* * * * *